(12) United States Patent
Heszler et al.

(10) Patent No.: US 10,456,899 B2
(45) Date of Patent: Oct. 29, 2019

(54) METHOD FOR SETTING AT LEAST ONE PARAMETER OF A HANDHELD POWER TOOL

(71) Applicant: Robert Bosch GmbH, Stuttgart (DE)

(72) Inventors: Anna Heszler, Schwieberdingen (DE); Florian Esenwein, Leinfelden-Echterdingen (DE); Joachim Schadow, Stuttgart (DE); Joern Stock, Wernau (DE)

(73) Assignee: Robert Bosch GmbH, Stuttgart (DE)

( * ) Notice: Subject to any disclaimer, the term of this patent is extended or adjusted under 35 U.S.C. 154(b) by 331 days.

(21) Appl. No.: 15/234,439

(22) Filed: Aug. 11, 2016

(65) Prior Publication Data

US 2017/0043471 A1 Feb. 16, 2017

(30) Foreign Application Priority Data

Aug. 12, 2015 (DE) ........................ 10 2015 215 362

(51) Int. Cl.
| | |
|---|---|
| *G06F 19/00* | (2018.01) |
| *B25F 5/00* | (2006.01) |
| *G06F 9/30* | (2018.01) |
| *G03G 15/00* | (2006.01) |
| *G02B 7/08* | (2006.01) |
| *G01N 35/00* | (2006.01) |

(52) U.S. Cl.
CPC ...... *B25F 5/00* (2013.01); *G01N 2035/00851* (2013.01); *G02B 7/08* (2013.01); *G03G 15/5075* (2013.01); *G05B 2219/39318* (2013.01); *G06F 9/30065* (2013.01)

(58) Field of Classification Search
CPC ............ B25F 5/00; G01N 2035/00851; G05B 2219/39318; G03G 15/5075; G06F 9/30065; G02B 7/08
USPC ........................................................ 700/160
See application file for complete search history.

(56) References Cited

U.S. PATENT DOCUMENTS

| | | | | |
|---|---|---|---|---|
| 6,428,487 B1 * | 8/2002 | Burdorff | ............ | A61B 10/0275 600/568 |
| 9,152,178 B2 * | 10/2015 | Koch | ...................... | G06F 1/206 |

(Continued)

FOREIGN PATENT DOCUMENTS

| | | |
|---|---|---|
| DE | 10 2012 202 116 A1 | 8/2013 |
| DE | 10 2012 211 580 A1 | 1/2014 |

(Continued)

*Primary Examiner* — Vu A Vu
(74) *Attorney, Agent, or Firm* — Maginot, Moore & Beck LLP

(57) ABSTRACT

A method for setting at least one parameter of a handheld power tool includes recording at least one first characteristic variable using at least one internal sensor unit or an external sensor unit and transmitting the first characteristic variable to at least one of (i) an internal data processing unit and (ii) an external data processing unit. The method further includes processing the first characteristic variable into at least one of (i) at least one first parameter output and (ii) an output of a combination of parameters and transmitting using a communication unit to at least one of (i) an internal open-loop and (ii) a closed-loop control unit. The method further includes calculating from the first parameter output at least one operating parameter of the handheld power tool and setting it on the handheld power tool.

15 Claims, 3 Drawing Sheets

(56) References Cited

U.S. PATENT DOCUMENTS

| | | | |
|---|---|---|---|
| 2011/0005792 A1* | 1/2011 | Matthias | B23Q 5/58 |
| | | | 173/170 |
| 2013/0193891 A1* | 8/2013 | Wood | H02P 7/06 |
| | | | 318/434 |
| 2013/0255980 A1* | 10/2013 | Linehan | B25F 5/00 |
| | | | 173/2 |
| 2015/0096018 A1* | 4/2015 | Mircescu | G06F 21/56 |
| | | | 726/23 |

FOREIGN PATENT DOCUMENTS

| | | |
|---|---|---|
| DE | 10 2013 206 166 A1 | 10/2014 |
| DE | 10 2013 212 635 A1 | 12/2014 |
| DE | 10 2014 209 009 A1 | 7/2015 |

* cited by examiner

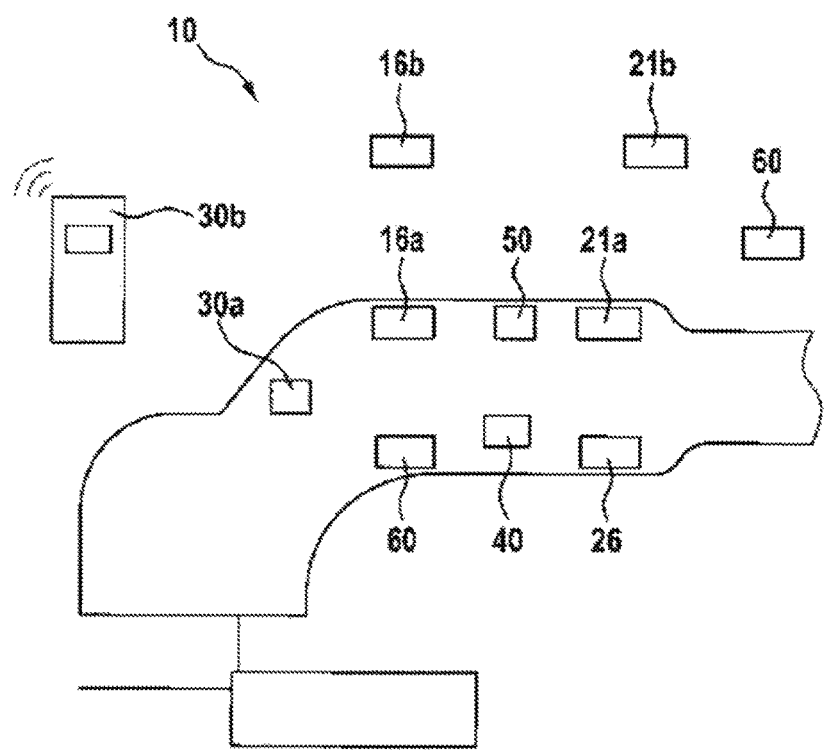

METHOD FOR SETTING AT LEAST ONE PARAMETER OF A HANDHELD POWER TOOL

This application claims priority under 35 U.S.C. § 119 to patent application no. DE 102015215362.2 filed on Aug. 12, 2015 in Germany, the disclosure of which is incorporated herein by reference in its entirety.

The disclosure relates to a method for setting at least one parameter of a handheld power tool.

SUMMARY

In the method for setting at least one parameter of a handheld power tool, at least one first characteristic variable is recorded by at least one internal sensor unit or an external sensor unit. An internal sensor unit is intended to be understood here as meaning a sensor unit that is arranged inside the handheld power tool. An external sensor unit is intended to be understood here as meaning a sensor unit that is arranged outside the handheld power tool.

The internal or external sensor may advantageously be configured at least as one of the following sensor applications: as an acceleration sensor, as a rotational rate sensor, as a pressure sensor, as an air pressure sensor, as a moisture sensor, as a gas sensor, as a position sensor, as a light sensor, as a proximity switch, as a sound sensor, as a temperature sensor, as a magnetic field sensor, as a location sensor, as a camera sensor, as an ultrasound sensor, as a radar, as a scanner or the like.

The first characteristic variable is advantageously transmitted to an internal data processing unit and/or to an external data processing unit. A data processing unit is intended to be understood as meaning in particular a component with a processor, a main memory and/or a program memory and also interfaces that make communication with the surroundings possible. Such a data processing unit may be for example an integrated circuit or a microcontroller. Stored in the data processing unit there may be libraries, in which characteristic variables, parameters, sets of parameters, images or the like are stored.

In the method according to the disclosure, the first characteristic variable is processed by the internal data processing unit and/or the external data processing unit and converted into at least one first parameter output and/or an output of a combination of parameters. A parameter output or a combination of parameters is intended to be understood here as meaning a preferred setting, a preferred operating point or a preferred application of the handheld power tool. This could be for example a vibration value, a removal capacity, an impact energy, an operating point at which the handheld power tool operates in an energy-saving mode, pulsed operation, broaching operation or the like.

Apart from a parameter or a combination of parameters, modes may also be produced. A mode is intended to be understood as meaning in particular a program and/or a machine setting that is suitable for the corresponding application, for example cutting of steel, grinding of stainless steel or the like.

The first parameter output and/or the output of a combination of parameters is transmitted from the internal data processing unit and/or the external data processing unit to an internal open-loop and/or closed-loop control unit. The device-internal open-loop and/or closed-loop control unit is intended in particular for calculating at least one operating parameter of the handheld power tool and setting it on the handheld power tool. An operating parameter is intended to be understood here as meaning in particular a manipulated variable for the handheld power tool.

In an alternative method for setting at least one parameter of a handheld power tool, at least one first characteristic variable is recorded by at least one internal sensor unit and at least one second characteristic variable is recorded by at least one external sensor unit. The first characteristic variable, recorded by the internal sensor unit, is advantageously transmitted to an internal data processing unit. The second characteristic variable, recorded by the external sensor unit, is advantageously transmitted to an external data processing unit. The first characteristic variable is processed by the internal data processing unit and converted into at least one first parameter output. The second characteristic variable is processed by the external data processing unit and converted into at least one second parameter output. The first parameter output and the second parameter output are preferably transmitted to a decision unit, which brings together the first parameter output and the second parameter output and makes a decision as to whether the first parameter output or the second parameter output is further processed. However, the decision may also be taken that both parameters are processed to form a new parameter or to form a new set of parameters.

The parameter output that is further processed is advantageously transmitted to an internal open-loop and/or closed-loop control unit. The internal open-loop and/or closed-loop control unit calculates from the parameter output that is further processed at least one operating parameter of the handheld power tool and sets the operating parameter on the handheld power tool.

Advantageous developments of the method according to the main claim are possible by the features presented in the subclaims.

The first characteristic variable may be for example an ambient characteristic variable. These are in particular a temperature characteristic variable, an atmospheric humidity characteristic variable, an emission characteristic variable, such as for example a dust-signal, a gas-signal, a noise-signal or an ambience-signal characteristic variable.

The first characteristic variable may be a machining tool characteristic variable. These are in particular a tool ID, a tool type, a diameter, a centrifugal mass, an inertial mass, a length or the like.

The first characteristic variable may be a workpiece characteristic variable or a material characteristic variable, wherein the workpiece characteristic variable or the material characteristic variable may be a strength, a resonant frequency, an elasticity, a shear strength, a density, an image or the like.

The first characteristic variable may be a work progress characteristic variable, wherein the work progress characteristic variable may be a removal rate, a drilling depth, a remaining length, a remaining width or the like.

The operating parameter is in particular a rotational speed, a torque, an impact energy, a current, a voltage or the like.

It is proposed that an information output takes place to an internal indicating device and/or an external indicating device.

An information output is intended to be understood as meaning that items of parameter information, state information, information concerning modes or the like are output to an internal indicating unit and/or an external indicating unit.

An indicating device is intended to be understood here as meaning in particular a device that indicates items of information optically, acoustically or the like.

An optical indicating device is intended to be understood here as meaning in particular a device that visually indicates the items of information by means of a light indicator, a digital indicator, a display or the like.

An acoustic indicating device is intended to be understood here as meaning in particular a device that audibly indicates the items of information by means of acoustic signals or the like.

It is proposed that a memory unit is intended for storing the first characteristic variable, the parameter output, the output of the combination of parameters and/or the operating parameters. A memory unit is intended to be understood here as meaning in particular an electronic memory unit that is intended for storing data electronically.

BRIEF DESCRIPTION OF THE DRAWINGS

Exemplary embodiments of the method according to the disclosure for setting at least one parameter of a handheld power tool are represented in the drawings, in which:

FIG. 3 shows a second embodiment of the handheld power tool with a second open-loop and/or closed-loop control circuit according to the disclosure.

DETAILED DESCRIPTION

Figure 1:
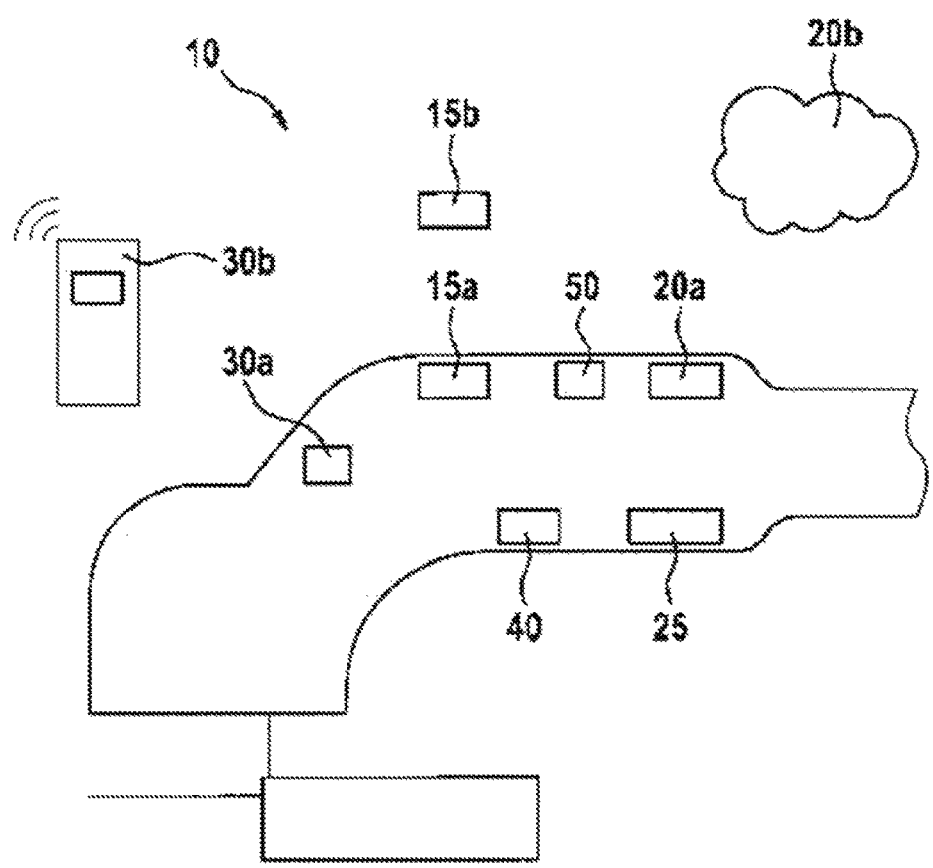
FIG. 1 shows a first embodiment of a handheld power tool with an open-loop and/or closed-loop control circuit according to the disclosure.

FIG. 1 shows a handheld power tool 10 with at least one internal sensor unit 15a, at least one external sensor unit 15b, at least one internal data processing unit 20a, at least one external data processing unit 20b and at least one internal open-loop and/or closed-loop control unit 25.

In a method for setting at least one parameter of the handheld power tool 10, a first characteristic variable is detected by the internal sensor unit 15a or the external sensor unit 15b. The first characteristic variable is transmitted to the internal data processing unit 20a and/or the external data processing unit 20b. The internal data processing unit 20a and/or the external data processing unit 20b processes the first characteristic variable and converts the first characteristic variable into a first parameter output and/or into an output of a combination of parameters.

In a configurational variant according to the disclosure, the internal sensor unit 15a or the external sensor unit 15b comprises an ambient sensor unit for recording an ambient characteristic variable. If the ambient sensor unit is a position sensor, a spatial alignment of the handheld power tool 10 is recorded. If the ambient sensor unit is an emission sensor, emissions of the handheld power tool 10 are recorded. Here, the emission sensor is intended for recording noise emissions, dust, sparks, pollutants or the like. If the ambient sensor unit is a moisture sensor, the atmospheric humidity in the ambience of the moisture sensor is recorded. If the ambient sensor unit is a temperature sensor, an ambient temperature is recorded.

Consequently, the ambient characteristic variable recorded by means of the ambient sensor unit, which may be a position characteristic variable, an emission characteristic variable, a moisture characteristic variable, a temperature characteristic variable or the like, is transmitted to the internal data processing unit 20a and/or the external data processing unit 20b.

In a further configurational variant according to the disclosure, the internal sensor unit 15a or the external sensor unit 15b comprises a machining tool sensor unit for recording a machining tool characteristic variable. The machining tool characteristic variable may be a tool ID, a tool type, a diameter, a centrifugal mass, an inertial mass, a length or the like.

Consequently, the machining tool characteristic variable recorded by means of the machining tool sensor unit, which may be a tool ID characteristic variable, a tool type characteristic variable, a diameter characteristic variable, a mass characteristic variable, a length characteristic variable or the like, is transmitted to the internal data processing unit 20a and/or the external data processing unit 20b.

In a further configurational variant according to the disclosure, the internal sensor unit 15a or the external sensor unit 15b comprises a workpiece sensor unit for recording a workpiece characteristic variable. The workpiece characteristic variable may be a strength, a resonant frequency, an elasticity, a shear strength or the like.

Consequently, the workpiece characteristic variable recorded by means of the workpiece sensor unit, which may be a strength characteristic variable, a resonant frequency characteristic variable, an elasticity characteristic variable, a shear strength characteristic variable or the like, is transmitted to the internal data processing unit 20a and/or the external data processing unit 20b.

The recording of the ambient characteristic variable, the machining tool characteristic variable and/or the workpiece characteristic variable by the ambient sensor unit, the machining tool sensor unit and/or the workpiece sensor unit may take place at the same time or at different times, at regular or irregular intervals at different points in time. Preferably, the ambient characteristic variable, the machining tool characteristic variable and/or the workpiece characteristic variable are recorded during the operation of the handheld power tool 10.

The internal data processing unit 20a and/or the external data processing unit 20b processes the ambient characteristic variable or the machining tool characteristic variable or the workpiece characteristic variable and converts the ambient characteristic variable or the machining tool characteristic variable or the workpiece characteristic variable into a first parameter output and/or into an output of a combination of parameters.

Apart from a parameter output, sets of parameters and/or modes may also be produced. A mode is intended to be understood as meaning in particular a program or a machine setting. The program or the machine setting is preferably suitable for a specific application, such as for example the cutting of steel, the grinding of stainless steel, the removal of flow material or the like.

The processing of the ambient characteristic variable, the machining tool characteristic variable and/or the workpiece characteristic variable by the internal data processing unit 20a and/or the external data processing unit 20b may take place at the same time or at different times, at regular or irregular intervals at different points in time. Preferably, the ambient characteristic variable, the machining tool characteristic variable and/or the workpiece characteristic variable are processed during the operation of the handheld power tool 10.

The first parameter output and/or the output of the combination of parameters is transmitted from the internal data processing unit 20a and/or the external data processing unit 20b to an internal open-loop and/or closed-loop control unit. The internal open-loop and/or closed-loop control unit calculates from the first parameter output at least one operating parameter of the handheld power tool and sets the operating parameter on the handheld power tool. The operating parameter may be in particular a rotational speed, a torque, an impact energy, a current, a voltage, a frequency, an advancement, a stroke of the machining tool or the like.

In the method according to the disclosure, items of information are transmitted by way of an information output to an internal indicating device 30a and/or an external indicating device 30b.

Items of information concerning parameters, operating parameters, sets of parameters, modes or operating states may be visually indicated by way of an optical indicating device. An optical indicating device may be an illumination device, a display, a projection device or the like. Items of information concerning parameters, operating parameters, sets of parameters, modes or operating states may be audibly indicated by way of an acoustic indicating device. An acoustic indicating device may be an acoustic signal transmitter, a loudspeaker or the like.

In the method according to the disclosure, the first characteristic variable, the parameter output, the output of the combination of parameters and/or the operating parameters are stored in a memory unit 40.

Figure 2:
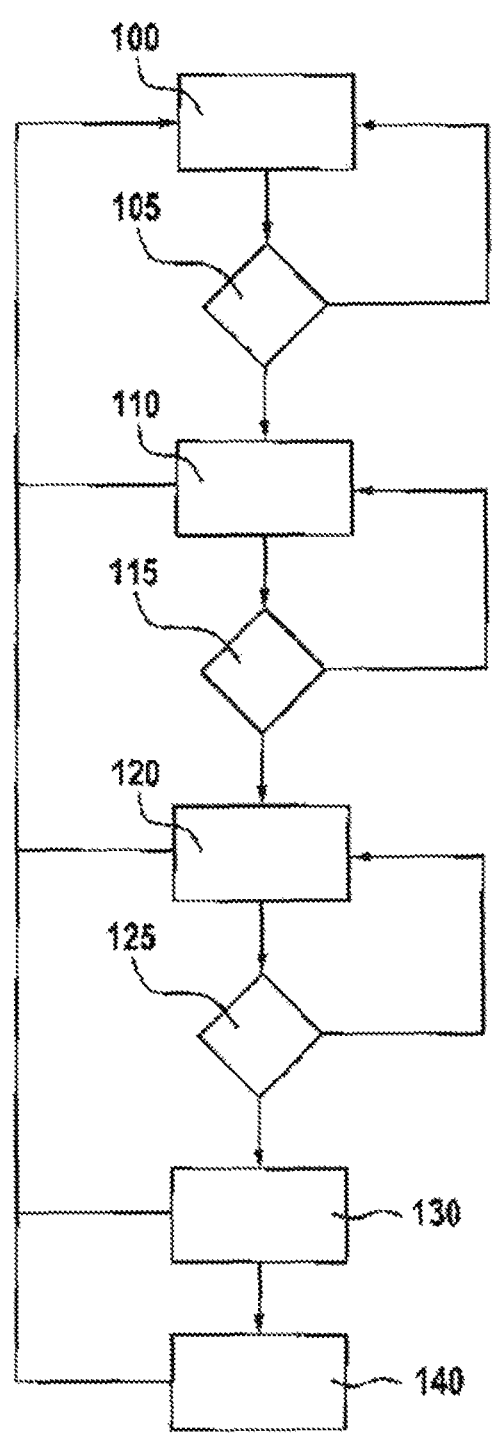
FIG. 2 shows a first flow diagram for setting a parameter of a handheld power tool.

FIG. 2 shows a flow diagram for the method for setting at least one parameter of the handheld power tool 10.

In the state 100, the method is in the starting state, that is to say that a handheld power tool 10 is in the switched-off state, or is idling or is in the load state. In the load state, the handheld power tool 10 is used in a working step. If in method step 105, in which the handheld power tool 10 is idling or is in the load state, a first characteristic variable is recorded by an internal sensor unit 15a or an external sensor unit 15b, in step 110 the first characteristic variable is transmitted to an internal data processing unit 20a and/or an external data processing unit 20b. If in step 115 the first characteristic variable has been transmitted completely, in step 120 the first characteristic variable is processed by the internal data processing unit 20a and/or the external data processing unit 20b and converted into at least one first parameter output and/or an output of a combination of parameters. However, it may also be that both parameters are processed to form a new parameter or to form a set of parameters. Once the data processing has been completed, in step 130 the first parameter output and/or the output of a combination of parameters is transmitted from the internal data processing unit 20a and/or the external data processing unit 20b to an internal open-loop and/or closed-loop control unit 25. In step 140, at least one operating parameter of the handheld power tool 10 is calculated with the aid of the internal open-loop and/or closed-loop control unit 25 from the first parameter output and set on the handheld power tool 10.

Furthermore, the first characteristic variable is recorded by the internal sensor unit 15, transmitted to the internal data processing unit 20. Furthermore, the first characteristic variable is processed by the internal data processing unit 20 and converted into a first parameter output and/or an output of a combination of parameters and transmitted from the internal data processing unit 20 to an internal open-loop and/or closed-loop control unit 25.

In an alternative method for setting at least one parameter of the handheld power tool 10 as shown in FIG. 3, at least one first characteristic variable is recorded by at least one internal sensor unit 16a and at least one second characteristic variable is recorded an external sensor unit 16b. The first characteristic variable, recorded by the internal sensor unit 16a, is transmitted to an internal data processing unit 21a and the second characteristic variable, recorded by the external sensor unit 16b, is transmitted to an external data processing unit 21b. The first characteristic variable is processed by the internal data processing unit 21a and converted into at least one first parameter output. The second characteristic variable is processed by the external data processing unit 21b and converted into at least one second parameter output. The first parameter output and the second parameter output are transmitted to a decision unit 60. The decision unit 60 brings together the first parameter output and the second parameter output and makes a decision as to whether the first parameter output or the second parameter output is further processed. The parameter output that is further processed is transmitted to an internal open-loop and/or closed-loop control unit 26. The internal open-loop and/or closed-loop control unit 26 calculates from the parameter output that is further processed at least one operating parameter of the handheld power tool 10 and sets the operating parameter on the handheld power tool 10.

What is claimed is:

1. A method for operating a handheld power tool according to at least one operating parameter, comprising:
   recording a first characteristic variable using an external sensor unit that is spaced apart from the power tool;
   transmitting the first characteristic variable to an external data processing unit that is spaced apart from the power tool;
   processing the first characteristic variable using the external data processing unit into at least one first parameter output;
   transmitting the at least one first parameter output from the external data processing unit to an internal control unit of the power tool;
   calculating at least one operating parameter of the handheld power tool using the internal control unit based on the at least one first parameter output;
   setting the at least one operating parameter on the power tool; and
   operating the power tool according to the at least one operating parameter that is based on the first characteristic variable,
   wherein the first characteristic variable is an ambient characteristic variable, and
   wherein the ambient characteristic variable is at least one of a temperature characteristic variable and an atmospheric humidity characteristic variable.

2. The method according to claim 1, wherein the at least one operating parameter is at least one of a rotational speed, a torque, an impact energy, a current, and a voltage.

3. The method according to claim 1, further comprising:
   transmitting the at least one operating parameter using an information output to at least one of (i) an internal indicating device and (ii) an external indicating device.

4. The method according to claim 3, further comprising:
   indicating the at least one operating parameter visually with an optical indicating device, or audibly with an acoustic indicating device.

5. The method according to claim 1, further comprising:
   storing in a memory unit at least one of the first characteristic variable, the at least one first parameter output, and the at least one operating parameter.

6. A method for operating a handheld power tool according to at least one operating parameter, comprising:
   recording a first characteristic variable using an external sensor unit that is spaced apart from the power tool;

transmitting the first characteristic variable to an external data processing unit that is spaced apart from the power tool;
processing the first characteristic variable using the external data processing unit into at least one first parameter output;
transmitting the at least one first parameter output from the external data processing unit to an internal control unit of the power tool;
calculating at least one operating parameter of the handheld power tool using the internal control unit based on the at least one first parameter output;
setting the at least one operating parameter on the power tool; and
operating the power tool according to the at least one operating parameter that is based on the first characteristic variable,
wherein the first characteristic variable is an ambient characteristic variable,
wherein the ambient characteristic variable is an emission characteristic variable, and
wherein the emission characteristic variable is at least one of a dust-signal, a gas-signal, a noise-signal, and an ambience-signal characteristic variable.

7. A method for operating a handheld power tool according to at least one operating parameter, comprising:
recording at least one first characteristic variable using at least one internal sensor unit and recording at least one second characteristic variable using at least one external sensor unit;
transmitting the first characteristic variable, recorded using the internal sensor unit, to an internal data processing unit and the second characteristic variable, recorded using the external sensor unit, to an external data processing unit;
processing the first characteristic variable using the internal data processing unit into at least one first parameter output and processing the second characteristic variable using the external data processing unit into at least one second parameter output;
transmitting the first parameter output and the second parameter output to a decision unit that is spaced apart from the power tool;
collecting the first parameter output and the second parameter output using the decision unit and determining whether the first parameter output or the second parameter output is further processed or both parameters are processed to form a new parameter or a set of parameters using the decision unit;
transmitting the first parameter output or the second parameter output that is further processed to at least one of (i) an internal open-loop and (ii) an closed-loop control unit;
calculating at least one operating parameter of the handheld power tool from the first parameter output or the second parameter output that is further processed using the at least one of (i) the internal open-loop and (ii) the closed-loop control unit;
setting the at least one operating parameter on the handheld power tool; and
operating the power tool according to the at least one operating parameter that is based on at least one of the first characteristic variable and the second characteristic variable.

8. The method according to claim 7, wherein:
the first characteristic variable is an ambient characteristic variable, and
the ambient characteristic variable is at least one of a temperature characteristic variable and an atmospheric humidity characteristic variable.

9. The method according to claim 7, wherein:
the first characteristic variable is an ambient characteristic variable,
the ambient characteristic variable is an emission characteristic variable, and
the emission characteristic variable is at least one of a dust-signal, a gas-signal, a noise-signal and an ambience-signal characteristic variable.

10. The method according to claim 7, wherein:
the first characteristic variable is a machining tool characteristic variable, and
the machining tool characteristic variable is at least one of a tool ID, a tool type, a diameter, a centrifugal mass, an inertial mass, and a length.

11. The method according to claim 7, wherein:
the first characteristic variable is a workpiece characteristic variable, and
the workpiece characteristic variable is at least one of a strength, a resonant frequency, an elasticity, and a shear strength.

12. The method according to claim 7, wherein the at least one operating parameter is at least one of a rotational speed, a torque, an impact energy, a current, and a voltage.

13. The method according to claim 7, further comprising:
transmitting the at least one operating parameter using an information output to at least one of (i) an internal indicating device and (ii) an external indicating device.

14. The method according to claim 13, further comprising:
indicating the at least one operating parameter visually with an optical indicating device, or audibly with an acoustic indicating device.

15. The method according to claim 7, further comprising:
storing in a memory unit at least one of the first characteristic variable, the at least one first parameter output, and the at least one operating parameter.

* * * * *